(12) United States Patent
Moinet et al.

(10) Patent No.: US 6,376,495 B1
(45) Date of Patent: Apr. 23, 2002

(54) ANTIDIABETIC PIPERAZINE DERIVATIVES, PROCESSES FOR THEIR PREPARATION AND COMPOSITIONS CONTAINING THEM

(75) Inventors: Gérard Moinet, Orsay; Dominique Marais, Meulan; Didier Mesangeau, Combs la Ville; Liliane Doare, Viry-Chatillon; Micheline Kergoat, Bures sur Yvette, all of (FR)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/744,693

(22) PCT Filed: Jul. 17, 1999

(86) PCT No.: PCT/EP99/05111

§ 371 Date: Jan. 29, 2001

§ 102(e) Date: Jan. 29, 2001

(87) PCT Pub. No.: WO00/06558

PCT Pub. Date: Feb. 10, 2000

(30) Foreign Application Priority Data

Jul. 28, 1998 (FR) .......................................... 98 09660

(51) Int. Cl.$^7$ .................. A61K 31/495; A61K 31/496; C07D 295/155; C07D 401/04; C07D 403/04
(52) U.S. Cl. ............................ 514/252.14; 514/253.01; 514/254.02; 514/254.06; 514/255.03; 544/295; 544/360; 544/368; 544/370; 544/394
(58) Field of Search ................................. 544/394, 360, 544/295, 368, 370; 514/252.14, 253.01, 254.02, 254.06, 255.03

(56) References Cited

U.S. PATENT DOCUMENTS 3,277,094 A * 10/1966 Werner ........................ 544/394
3,951,983 A     4/1976 Danilewicz et al.
5,464,788 A * 11/1995 Bock et al. .................. 544/360

FOREIGN PATENT DOCUMENTS

EP          0173634         3/1986

\* cited by examiner

*Primary Examiner*—Emily Bernhardt
(74) *Attorney, Agent, or Firm*—Millen, White, Zelano & Branigan, P.C.

(57) ABSTRACT

Piperazine derivatives of formula (I)

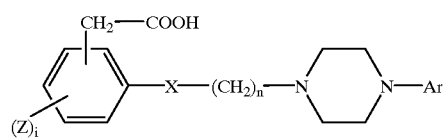

wherein

Z, X, n, Ar and i have the meanings defined herein are usefull in the treatment of pathologies associated with insulin-resistance syndrome.

23 Claims, No Drawings

ANTIDIABETIC PIPERAZINE DERIVATIVES, PROCESSES FOR THEIR PREPARATION AND COMPOSITIONS CONTAINING THEM

The present invention relates to novel piperazine derivatives which are of use in the treatment of pathologies associated with insulin-resistance syndrome.

The compounds of the invention have the formula:

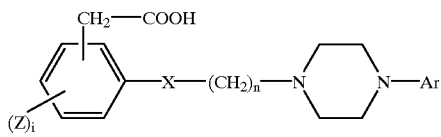

in which:

n represents 2, 3, 4, 5 or 6;

X represents O or S;

Ar represents an aromatic nucleus chosen from phenyl, pyridyl, pyrimidinyl, benzoxazolyl, benzothiazolyl and benzimidazolyl, the said aromatic nucleus optionally being substituted by one or more radicals chosen from a halogen atom; a $(C_1-C_6)$ alkoxy group; a $(C_6-C_{10})$ aryloxy group; a $(C_6-C_{10})$aryl$(C_1-C_6)$alkoxy group in which the aryl part is optionally substituted by halogen, $(C_1-C_6)$alkyl or $(C_1-C_6)$alkoxy; and a $(C_1-C_6)$alkyl group substituted by one or more halogen atoms;

i represents 0, 1, 2, 3 or 4; and each Z group independently represents a halogen atom; as well as their addition salts with pharmaceutically acceptable bases or acids.

The invention also relates to the solvates of the compounds of formula I.

The term "alkyl" is understood to mean, according to the invention, a linear or branched hydrocarbon-comprising group. Mention may be made, as example of alkyl groups, of the methyl, ethyl, propyl, n-butyl, isobutyl, sec-butyl, tert-butyl, isoamyl, tert-amyl, sec-amyl, pentyl and hexyl groups.

The alkyl parts of the alkoxy and arylalkoxy groups have the same definition as given above for the alkyl group.

Mention may be made, as example of alkyl groups substituted by one or more halogen atoms, of the perfluoroalkyl groups, such as trifluoromethyl or pentafluoroethyl.

The aryl group is a mono- or polycyclic aromatic group, preferably mono- or bicyclic, such as phenyl or naphthyl. The same definition is valid for the aryl parts of the aryloxy and arylalkoxy groups.

The halogen atoms are chosen from bromine, fluorine, iodine and chlorine.

When Ar represents substituted phenyl, the phenyl nucleus can carry one, two, three, four or five substituents. However, when Ar represents substituted phenyl, the phenyl nucleus is preferably mono-, di- or trisubstituted. In this case, the substituents are preferably in the meta or para position.

Examples of preferred aryloxy groups are phenoxy and naphthyloxy.

An example of a preferred arylalkoxy group is the benzyloxy group.

The —CH$_2$—COOH group of the compounds of the invention is situated either in the ortho position or in the meta position or in the para position with regard to the chain

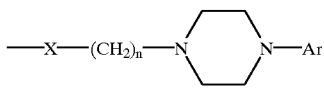

However, preference is given to the compounds in which the —CH$_2$—COOH group is in the para or ortho position, the para position being especially preferred.

The compounds of formula I have a carboxyl functional group and can be salified. They are then provided in the form of addition salts with organic or inorganic bases.

The addition salts with bases are, for example, pharmaceutically acceptable salts, such as the sodium salts, the potassium salts or the calcium salts, which are obtained by using the corresponding alkali metal or alkaline earth metal hydroxides as bases.

Mention may be made, as other types of addition salts with pharmaceutically acceptable bases, of the salts with amines and in particular glucamine, N-methylglucamine, N,N-dimethylglucamine, ethanolamine, morpholine, N-methylmorpholine or lysine.

The compounds of formula I can also be salified with inorganic or organic acids and preferably pharmaceutically acceptable acids, such as hydrochloric acid, phosphoric acid, fumaric acid, citric acid, oxalic acid, sulphuric acid, ascorbic acid, tartaric acid, maleic acid, mandelic acid, methanesulphonic acid, lactobionic acid, gluconic acid, glucaric acid, succinic acid, sulphonic acid or hydroxypropane-sulphonic acid.

The salts of the compounds of formula I with acids and bases which are not pharmaceutically acceptable form another aspect of the invention. These salts are intermediate compounds of use in the preparation of the compounds of the invention. This is because the compounds of the invention can be isolated as intermediates in the form of one of their non-pharmaceutically acceptable salts, before conversion to a pharmaceutically acceptable compound.

A first group of preferred compounds is composed of the compounds of formula I in which X represents an oxygen atom.

Preference is more particularly given, among the compounds of the invention, to those in which n represents 2 or 3 and better still those in which n is 2.

Another group of preferred compounds is composed of the compounds in which Ar represents unsubstituted pyridyl, unsubstituted pyrimidinyl or optionally substituted phenyl. When Ar represents substituted phenyl, the phenyl group preferably carries one or two substituents chosen from $(C_1-C_6)$alkoxy, halogen, phenoxy, trifluoromethyl and benzyloxy. Better still, when Ar represents substituted phenyl, the phenyl group is substituted in the meta position by a $(C_1-C_6)$alkoxy group, a phenoxy group, a trifluoromethyl group or a halogen atom, such as a fluorine or chlorine atom.

Another group of preferred compounds is composed of the compounds of formula I in which i represents 1 or 0, preferably 0.

According to a preferred alternative form of the invention, when i is 1, the —CH$_2$—COOH group is situated in the ortho position with regard to the chain

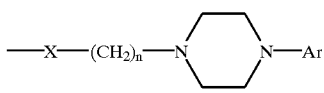

and the Z substituent is in the para position with respect to this same chain.

A final group of preferred compounds is composed of the compounds of formula I in which the —CH$_2$—COOH group is situated in the para position on the phenyl group with respect to the chain

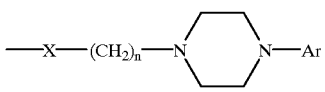

The invention also relates to two processes for the preparation of the compounds of formula I.

According to a first process, an aromatic compound of formula II:

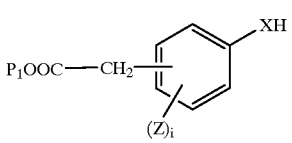

in which Z, X and i are as defined above for the formula I and P$_1$ is a protective group for a carboxyl functional group, is reacted with a piperazine of formula III:

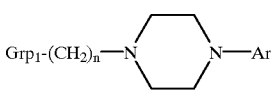

in which n and Ar are as defined above for the formula I and Grp$_1$ is a leaving group.

Among the protective groups for carboxyl functional groups, those generally described in Protective Groups in Organic Synthesis, Greene T. W. and Wuts P. G. M., published by John Wiley and Sons, 1991, and in Protective Groups, Kocienski P. J., 1994, Georg Thieme Verlag, may be suitable. It is possible, by way of example, to envisage the protection of the carboxyl functional group in the ester form: in this case, P$_1$ represents (C$_1$–C$_6$)alkyl.

A halogen atom (for example chlorine or bromine), a (C$_6$–C$_{10}$)arylsulphonyloxy group, in which the aryl group is optionally substituted by one or more (C$_1$–C$_6$)alkyl groups, or a (C$_1$–C$_6$)alkylsulphonyloxy group, in which the alkyl group is optionally substituted by one or more halogen atoms, may be selected as example of a Grp$_1$ group.

The operating conditions for the reaction of the compound II with the piperazine III will be easily determined by a person skilled in the art, this reaction being a nucleophilic substitution.

The reaction of the compound II with the piperazine III is advantageously carried out in a polar aprotic solvent in the presence of a base.

Examples of appropriate solvents are acetonitrile, dimethylformamide, acetone, dimethyl sulphoxide and halogenated hydrocarbons, such as dichloromethane or dichloroethane.

Use may be made, as particularly preferred base, of potassium carbonate.

According to a preferred embodiment, the reaction of II with III is carried out at a temperature of 50 to 120° C., for example at reflux of acetonitrile, when the latter is chosen as solvent, in the presence of an alkali metal iodide, such as potassium iodide.

The amount of potassium iodide which has to be used is variable and depends essentially on the nature of the reactants, on the nature of the solvent and on the reaction temperature.

A catalytic amount of potassium iodide (less than 1 molar equivalent with respect to the compound II) is generally sufficient.

The reaction of the compound II with the compound III is stoichiometric. However, it may be possible to carry out the reaction in the presence of a slight excess of the piperazine III, in such a way that the molar ratio of III to II will generally be between 1 and 1.2.

The reaction of the compound II with the piperazine III leads to a compound of formula IV:

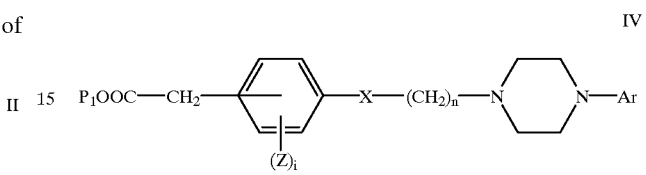

in which P$_1$, X, Z, i, n and Ar are as defined above, which compound is converted to a compound of formula I by deprotection of the carboxyl functional group.

The deprotection methods are those commonly used in the art. They are, for example, described in Protective Groups in Organic Synthesis, Green T. W. and Wuts P. G. M., published by John Wiley and Sons, 1991, and in Protective Groups, Kocienski P. J., 1994, Georg Thieme Verlag.

When P$_1$ represents (C$_1$–C$_6$)alkyl, the deprotection can involve the saponification of the ester functional group, for example by the action of dilute sodium hydroxide solution.

The compounds of formula II are generally commercially available or easily prepared by following known techniques.

The compounds of formula III can be prepared by reaction of a piperazine of formula V:

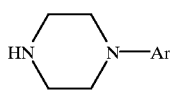

in which Ar is as defined above, with a compound of formula VIII:

where Grp$_1$ is as defined above and T is a leaving group identical to or different from Grp$_1$ and preferably a better nucleofuge than Grp$_1$, A person skilled in the art knows in particular that a leaving group becomes increasingly labile as the corresponding negatively charged species resulting from the heterolytic cleavage of the bond increases in stability. In this particular instance, T$^-$ must be more stable than Grp$_1^-$ in order for T to be a better nucleofuge than Grp$_1$.

According to a preferred alternative form of the invention, Grp$_1$ is a chlorine atom and T is a bromine atom.

The reaction of V with VIII is preferably carried out in a polar aprotic solvent chosen from those defined above, at a temperature of between 15 and 80° C., preferably between 15 and 35° C., for example at room temperature (20 to 25° C.). Dimethylformamide is preferred, by way of solvents.

The reaction of the piperazine V with the compound VIII advantageously takes place in the presence of a base, such as potassium carbonate.

Another process of for the preparation of the compounds of formula I consist in reacting a piperazine of formula V

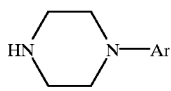

in which Ar is as defined above for the formula I, with a carboxyl derivative of formula VI

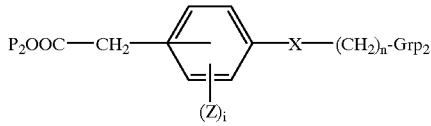

in which n, X, Z and i are as defined above for the formula I, $P_2$ is a protective group for a carboxyl functional group and $Grp_2$ represents a leaving group. $P_2$ may take any one of the meanings of $P_1$ above. Just as for $P_1$, it is preferable for $P_2$ to represent $(C_1-C_6)$alkyl. $Grp_2$ is a leaving group, the meaning of which is not critical according to the invention. $Grp_2$ can usually represent a halogen atom, a $(C_6-C_{10})$aryl-sulphonyloxy group, in which the aryl part is optionally substituted by one or more $(C_1-C_6)$alkyl groups, or a $(C_1-C_6)$alkylsulphonyloxy group, in which the alkyl group is optionally substituted by one or more halogen atoms.

The reaction of the piperazine V with the compound VI may be carried out in any one of the polar aprotic solvents defined above, preferably in acetonitrile. The yields and the kinetics of the reaction are markedly improved when the reaction is carried out in the presence of a base and in particular in the presence of potassium carbonate.

The reaction may be carried out at a temperature of between 50 and 120° C., for example at reflux of the acetonitrile, when the latter acts as solvent.

By way of example, the piperazine of formula V is reacted with at least one equivalent of the compound of formula VI, in acetonitrile, in the presence of 1.5 to 3 equivalents of $K_2CO_3$ with respect to the piperazine of formula V. The molar ratio of the compound of formula VI to the piperazine V is advantageously between 1 and 1.5, preferably between 1 and 1.2.

According to a preferred embodiment of the invention, the reaction of V with VI is carried out in the presence of an alkali metal iodide, such as potassium iodide. It can be of use to use up to 1 equivalent of alkali metal iodide with respect to the amount of piperazine V. Thus, the molar ratio of alkali metal iodide to the piperazine V may vary between 0.1 and 1.5 equivalents.

The reaction of the piperazine V with the compound VI results in a compound of formula VII:

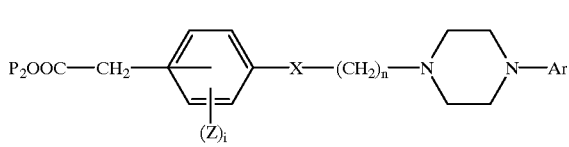

in which n, X, Z, Ar, i and $P_2$ are as defined above, which compound is converted to a compound of formula I by deprotection of the carboxyl functional group.

The operating conditions for the deprotection reaction will be easily determined by a person skilled in the art according to the nature of the $P_2$ group.

When $P_2$ represents $(C_1-C_6)$alkyl, the deprotection can involve the saponification of the ester functional group, for example by the action of dilute sodium hydroxide solution.

The compounds of formula V are commercially available or easily prepared from commercial compounds.

The compounds of formula VI are easily prepared by reaction of a compound of formula IX

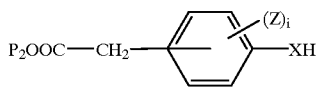

in which $P_2$, X, Z and i are as defined above for the formula VI, with a derivative of formula X

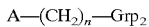

where n and $Grp_2$ are as defined above for the formula VI and A represents a leaving group identical to or different from $Grp_2$ and preferably more nucleofugic than $Grp_2$. According to a preferred embodiment of the invention, A is a bromine atom and $Grp_2$ is a chlorine atom.

The operating conditions for this reaction will be easily determined by a person skilled in the art using his overall knowledge of organic chemistry.

The reaction of IX with X preferably takes place in a polar aprotic solvent in the presence of a base, at a temperature of between 15 and 120° C.

By way of example, the compound IX may be reacted with 1 to 4 equivalents, preferably 1.4 to 3 equivalents, of the derivative X in acetonitrile, as solvent, in the presence of 1.5 to 3.5 equivalents of $K_2CO_3$ with respect to the amount of compound IX, at a temperature of between 40 and 120° C. The molar ratio of $K_2CO_3$ to the compound X is advantageously between 0.8 and 1.2.

The compounds of the invention are of use in the treatment of pathologies associated with insulin-resistance syndrome (syndrome X).

Insulin resistance is characterized by a reduction in the action of insulin (cf. Presse Medicale, 1997, 26 (No. 14), 671–677) and is implicated in a large number of pathological conditions, such as diabetes and more particularly non-insulin-dependent diabetes (type II diabetes or NIDDM), dyslipidaemia, obesity, arterial hypertension and certain microvascular and macrovascular complications, such as atherosclerosis, retinopathies and neuropathies.

Reference may be made, in this respect, to, for example, Diabetes, Vol. 37, 1988, 1595–1607, Journal of Diabetes and its Complications, 1998, 12, 110–119, or Horm. Res., 1992, 38, 28–32.

The compounds of the invention in particular exhibit a strong hypoglycaemic or hypolipidaemic activity.

Another subject-matter of the present invention is therefore pharmaceutical compositions comprising, as active principle, a compound according to the invention.

The pharmacuetical compositions according to the invention can be presented in forms intended for administration by the parenteral, oral, rectal, permucosal or percutaneous route.

They will therefore be presented in the form of injectable solutions or suspensions or multi-dose bottles, in the form of coated or uncoated tablets, of dragees, of capsules, including hard gelatin capsules, of pills, of cachets, of powders, of suppositories or of rectal capsules, of solutions or of suspensions, for percutaneous use, in a polar solvent, for permucosal use.

The excipients which are suitable for such administrations are derivatives of cellulose or micro-crystalline cellulose, alkaline earth carbonates, magnesium phosphate, starches, modified starches or lactose for the solid forms.

For rectal use, cocoa butter or polyethylene glycol stearates are the preferred excipients.

For parenteral use, water, aqueous solutions, physiological saline or isotonic solutions are the most conveniently used vehicles.

The dosage can vary within wide limits according to the therapeutic indication and the administration route, as well as the age and the weight of the subject.

The invention therefore also relates to the use of the compounds of formula I in the preparation of medicaments intended for the treatment of diabetes.

The following examples illustrate the preparation of the compounds of formula I and that of the intermediates of formulae III and VI.

In the continuation, the following abbreviations have been used:

NMR: nuclear magnetic resonance
δ: chemical shift
s: singlet
d: doublet
t: triplet
m: unresolved peak
IR: infrared.

A—EXAMPLE OF THE PREPARATION OF A COMPOUND OF FORMULA III

Preparation of 1-(2-chloroethyl)-4-phenylpiperazine (III: $Grp_1$=Cl, n=2, Ar=$C_6H_5$)

358.52 g of 1-bromo-2-chloroethane are added to 80 ml of dry dimethylformamide at 20° C. in a three-necked flask equipped with a mechanical stirrer, followed by 138 g of potassium carbonate and 81.12 g of N-phenylpiperazine dissolved in 300 ml of dimethylformamide. The reaction mixture is then stirred for 2 h 30 at room temperature. It is subsequently poured onto 1 liter of a saturated aqueous sodium chloride solution and extracted with diethyl ether. The organic phases are combined and evaporated. 67 g of a yellow oil are obtained, which oil is purified on a silica cake by using ethyl acetate as eluent. NMR (200 MHz), $CDCl_3$, δ ppm: 2.68 (t, 4H), 2.80 (t, 2H), 3.25 (t, 4H), 3.64 (t, 2H), 6.93 (m, 3H), 7.28 (t, 2H) IR (cm$^{-1}$); film: 2677, 1593, 1297.

B—EXAMPLES OF THE PREPARATION OF COMPOUNDS OF FORMULA VI

1—Preparation of methyl [4-(2-chloroethoxy)-phenyl]acetate
(VI: $Grp_2$=Cl, n=2, i=0, $P_2$=$CH_3$)

100 g of methyl [4-hydroxyphenyl]acetate and 248.6 g of potassium carbonate are added, with mechanical stirring, to a three-necked flask containing 900 ml of acetonitrile. The reaction mixture is brought to 50° C. and 258.13 g of 1-bromo-2-chloroethane, dissolved in 250 ml of acetonitrile, are added over 1 hour. The reaction mixture is then brought to reflux of the solvent for 48 h.

After filtering the reaction mixture, the solvent is evaporated. The residual oil is taken up in a mixture of water and diethyl ether. The ethereal phases are combined, washed with normal sodium hydroxide solution and then washed several times with water. After drying and evaporating the solvent, a greyish oil is obtained which is then purified by distillation (boiling point at 0.1 mm of mercury=112–116° C.). NMR (200 MHz), $CDCl_3$, δ ppm: 3.60 (s, 2H), 3.70 (s, 3H), 3.82 (t, 2H), 4.25 (t, 2H), 6.85 (d, 2H), 7.22 (d, 2H) IR (cm$^{-1}$); film: 2953, 1736, 1513, 1243.

The intermediates of formula VI, VI.2 to VI.6, collated in the following Table 1 are prepared and isolated in an analogous way.

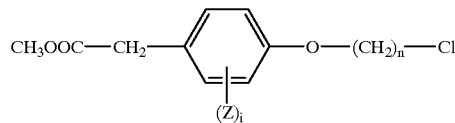

TABLE 1

| Intermediate compound | Position of the $CH_2$-COOH group | i | Z | n | M.p. (° C.)/ B.p. (° C.) |
|---|---|---|---|---|---|
| VI. 2 | p | 0 | / | 2 | B.p. = 112–116° C.[a] |
| VI. 3 | m | 0 | / | 2 | oil |
| VI. 4 | o | 0 | / | 2 | oil |
| VI. 5 | p | 0 | / | 3 | oil |
| VI. 6 | p | 0 | / | 4 | oil |

[a]boiling point at 0.1 mm Hg

In the above table, o, m and p respectively mean ortho, meta and para.

The position of the —$CH_2$—COOH group is indicated with respect to the —O—$(CH_2)_n$—Cl chain.

The position of the Z substituent is also indicated with respect to the —O—$(CH_2)_n$—Cl chain.

C—EXAMPLES OF THE PREPARATION OF COMPOUNDS OF FORMULA I

1—Preparation of (4-{2-[4-(3-methoxyphenyl)-piperazin-1-yl]ethoxy}phenyl) acetic acid (Example 1)

[I: Ar=—$C_6H_4$—$OCH_3$, n=2, i=0]

34.6 g of 1-(3-methoxy)phenylpiperazine [sic], 74.52 g of potassium carbonate and 29.88 g of potassium iodide are added, with magnetic stirring, to a three-necked flask containing 400 ml of acetonitrile. 41.16 g of methyl [4-(2-chloroethoxy)phenyl]acetate, dissolved in 250 ml of acetonitrile, are subsequently introduced over 15 min. The reaction mixture is maintained at reflux of the solvent for 72 h. After returning to room temperature, the reaction mixture is filtered and the solvent is evaporated. The residue is taken up in a mixture of water and ethyl acetate. The combined organic phases are then dried and then evaporated. 48.79 g of an orangey oil are thus isolated.

400 ml of methanol and 189.2 ml of 1N sodium hydroxide solution are added to the latter. The reaction mixture is then maintained for 2 h at reflux of the solvent. After evaporation of the solvent to dryness, the residue is triturated several times with diethyl ether. After removing the ethereal phases, 1 liter of water is added to the residue. After stirring for 10 min, 189.2 ml of 1N hydrochloric acid are added. A beige precipitate is formed. After filtering off this precipitate and washing with water of the reaction mixture and then drying, 42 g of a solid are obtained. The recrystallization from ethanol at 95° C. [sic], 38 g of the title compound are obtained, the melting point of which is between 156 and 158° C. NMR (200 MHz), d6-DMSO, δ ppm: 2.48 (t, 4H), 2.60 (t, 2H), 2.95 (t, 4H), 3.35 (s, 2H), 3.60 (s, 3H), 3.95 (t, 2H), 6.30 (m, 3H), 6.70 (d, 2H), 7.0 (m, 3H) IR (cm$^{-1}$); KBr: 2957, 1716, 1597, 1604, 1242.

The compounds of Examples 2 to 19 which appear in the following Table 2, where X in the formula below represents O:

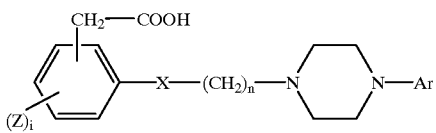

are prepared by using one of the processes described above.

TABLE 2

| Ex. | Position of —CH$_2$—COOH | i | Z | n | Ar | Melting point (° C.) | $^1$H NMR (200 MHz) δ (ppm) |
|---|---|---|---|---|---|---|---|
| 1 | para | 0 | — | 2 | 2-methoxyphenyl | 158–160 | d6-DMSO: 2.48(t, 4H), 2.60(t, 2H), 2.9 (t, 4H), 3.35(s, 2H), 3.60(s, 3H), 3.95 (t, 2H), 6.30(m, 3H), 6.70(d, 2H), 7.0 (m, 3H) |
| 2 | para | 0 | — | 2 | phenyl | 163 | d6-DMSO: 2.54(t, 4H), 2.62(t, 2H), 3.0 (t, 4H), 3.36(s, 2H), 3.98(t, 2H), 6.68 (t, 1H), 6.80(t, 4H), 7.04(m, 4H) |
| 3 | ortho | 0 | — | 2 | 2-methoxyphenyl | 74–76 | d6-DMSO: 2.50(s, 4H), 2.65(t, 2H), 3.07 (s, 4H), 3.40(s, 2H), 3.62(s, 3H), 4.05 (s, 2H), 6.30(m, 3H), 6.95(m, 5H) |
| 4 | meta | 0 | — | 2 | 3-methoxyphenyl | 110–111 | d6-DMSO: 2.45(s, 4H), 2.95(s, 4H), 3.35 (s, 2H), 3.50(s, 3H), 3.90(t, 2H), 6.20 (m, 3H), 6.62(d, 3H), 6.91(m, 2H) |
| 5 | para | 0 | — | 2 | 2-(benzyloxy)phenyl | 130 | d6-DMSO: 2.72(s, 4H), 2.88(t, 2H), 3.20 (s, 4H), 3.55(s, 2H), 4.15(t, 2H), 5.12 (s, 2H), 6.60(s+d, 3H), 7.0(d, 2H), 7.25 (m, 3H), 7.50(m, 5H), 12.30(s, 1H) |
| 6 | para | 0 | — | 2 | 2-chlorophenyl | 130–132 | CDCl3 [sic]: 2.77(m, 6H), 3.13(d, 4H), 3.35(s, 2H), 3.96(t, 2H), 6.67(m, 5H), 7.03(m, 3H), 10.35(s, 1H) |
| 7 | para | 0 | — | 2 | 4-methoxyphenyl | 162–164 | d6-DMSO: 2.65(s, 4H), 2.77(t, 2H), 3.07 (s, 4H), 3.55(s, 2H), 3.73(s, 3H), 4.11 (t, 2H), 6.95(m, 6H), 7.22(d, 2H) |
| 8 | para | 0 | — | 2 | 3-phenoxyphenyl | 160–163 | CDCl3 [sic]: 2.7(m, 6H), 3.12(m, 4H), 3.40 (s, 2H), 4.0(t, 2H), 6.50(m, 5H), 7.00 (m, 8H), 7.82(s, 1H) |

TABLE 2-continued

| Ex. | Position of —CH₂—COOH | i | Z | n | Ar | Melting point (° C.) | ¹H NMR (200 MHz) δ (ppm) |
|---|---|---|---|---|---|---|---|
| 9 | para | 0 | — | 2 | 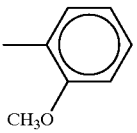 | 204–206 (2HCl) | d6-DMSO: 3.35(m, 12H), 3.75(s, 3H), 4.45 (s, 2H), 6.90(m, 6H), 7.15(d, 2H), 9.40 (s, 2H), 11.65(s, 1H) |
| 10 | para | 0 | — | 2 | 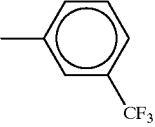 | 134–136 | d6-DMSO: 2.51(s, 4H), 2.65(t, 2H), 3.15 (s, 4H), 3.40(s, 2H), 4.0(t, 2H), 6.75 (d, 2H), 6.95(m, 5H), 7.08(t, 1H) |
| 11 | para | 0 | — | 2 | 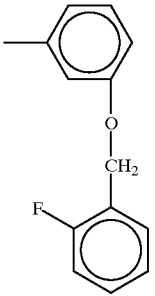 | 140 | d6-DMSO: 2.67(s, 4H), 2.75(t, 2H), 3.18 (s, 4H), 3.50(s, 2H), 4.10(t, 2H), 5.12 (s, 2H), 6.45(m, 3H), 6.90(d, 2H), 7.20 (m, 5H), 7.45(t, 1H), 7.65(t, 1H) |
| 12 | para | 0 | — | 2 | 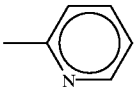 | 132–134 | d6-DMSO: 2.56(t, 4H), 2.77(t, 2H), 3.50 (d, 6H), 4.10(t, 2H), 6.39(t, 1H), 6.87 (m, 3H), 7.22(d, 2H), 7.58(t, 1H), 8.14 (d, 1H), 12.85(s, 1H) |
| 13 | para | 0 | — | 2 |  | 153–154 | CDCl3 [sic]: 2.95(t, 4H), 3.10(t, 2H), 3.64(s, 2H), 4.09(t, 4H), 4.24(t, 2H), 6.59(t, 1H), 6.83(d, 2H), 7.28(d, 2H), 8.44(d, 2H), 9.22(s, 1H) |
| 14 | para | 0 | — | 4 | 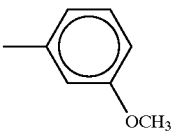 | 113–115 | CDCl3 [sic]: 1.75(s, 4H), 2.73(s, 2H), 2.95(s, 4H), 3.37(s, 4H), 3.60(s, 2H), 3.85(s, 5H), 6.50(m, 3H), 6.80(d, 2H), 7.25(q, 3H), 8.30(s, 1H) |
| 15 | para | 0 | — | 2 | 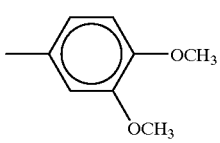 | 135–137 | CDCl3 [sic]: 2.82(s, 6H), 3.05(s, 4H), 3.40(s, 6H), 4.0(s, 2H), 6.42(m, 2H), 6.67(t, 3H), 7.10(d, 2H), 11.80(s, 1H) |
| 16 | para | 0 | — | 3 | 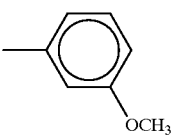 | 162–164 | d6-DMSO: 1.90(t, 2H), 2.47(s, 6H), 3.10 (s, 4H), 3.45(s, 2H), 3.65(s, 3H), 3.95 (t, 2H), 6.40(m, 3H), 6.85(d, 2H), 7.15 (m, 3H) |
| 17 | para | 0 | — | 2 | 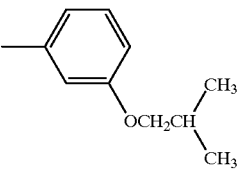 | 148 | d6-DMSO: 0.83(d, 6H), 1.85(m, 1H), 2.44 (s, 4H), 2.74(t, 2H), 3.13(s, 4H), 3.34 (s, 2H), 3.55(d, 2H), 3.94(t, 2H), 6.27 (m, 3H), 6.74(d, 2H), 6.98(m, 3H) |

TABLE 2-continued

| Ex. | Position of —CH$_2$—COOH | i | Z | n | Ar | Melting point (° C.) | $^1$H NMR (200 MHz) δ (ppm) |
|---|---|---|---|---|---|---|---|
| 18 | para | 0 | — | 2 | 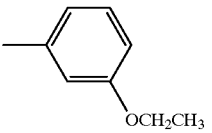 | 153–154 | d6-DMSO: 1.14(t, 3H), 2.46(s, 4H), 2.58 (t, 2H), 2.96(s, 4H), 3.35(s, 2H), 3.81 (q, 2H), 3.94(t, 2H), 6.27(m, 3H), 6.74 (d, 2H), 6.92(m, 3H) |
| 19 | para | 0 | — | 2 | 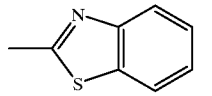 | 160–162 | d6-DMSO: 2.65(s, 4H), 2.79(t, 2H), 3.52 (s, 2H), 3.59(s, 4H), 4.11(t, 2H), 6.92 (d, 2H), 7.18(m, 4H), 7.50(d, 1H), 7.78 (d, 1H), 12.30(s, 1H) |

Likewise, the following compound 20 is prepared by employing a process analogous to those illustrated above:

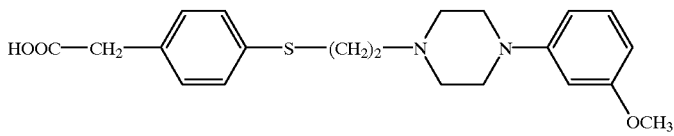

which compound has a melting point of 142° C. and is characterized by the following soectral data: d6-DMSO: 2.43 (t, 6H), 2.99 (t, 6H), 3.42 (s, 2H), 3.59 (s, 3H), 6.32 (m, 3H), 7.11 (m, 5H).

The results of a pharmacological study will be given below.

Study of the Antidiabetic Activity in the Rat

The antidiabetic activity of the compounds of formula I by the oral route was determined on an experimental model of non-insulin-dependent diabetes induced in the rat by streptozotocin.

The model of non-insulin-dependent diabetes is obtained in the rat by a neonatal injection (on the day of birth) of streptozotocin.

The diabetic rats used are 8 weeks old. The animals are kept, from the day of their birth to the day of the experiment, in an animal house at a regulated temperature of 21 to 22° C. and are subjected to a fixed cycle of light (from 7 h to 19 h) and of darkness (from 19 h to 7 h). Their diet consisted of a maintenance diet; water and food were provided "ad libitum", with the exception of the 2 hours of fasting preceding the tests, where food is withdrawn (post-absorptive state).

The rats are treated by the oral route, during the day, with the test product. Two hours after the final administration of the product and 30 minutes after anaesthetizing the animals with sodium pentobarbital (Nembutal®), a 300-μl blood sample is withdrawn at the end of the tail in order to determine the glycaemia.

The results obtained are collated in Table 3.

These results are expressed as a percentage of change in the glycaemia:
at D1 (after treatment for 1 day) with respect to D0 (before treatment); and
at D4 (after treatment for 4 days) with respect to D0 (before treatment) for 2 different administration doses (20 mg/kg/day and 200 mg/kg/day) of active principle.

TABLE 3

| Compound of Example | Dose administered 20 mg/kg/day | | Dose administered 200 mg/kg/day | |
|---|---|---|---|---|
| | % of glycaemia at D1 | % of glycaemia at D4 | % of glycaemia at D1 | % of glycaemia at D4 |
| 1 | −8 | −10 | −24 | −34 |
| 4 | −2 | −16 | −20 | −24 |
| 6 | 2 | −12 | −2 | −19 |
| 8 | 9 | −6 | 19 | −18 |
| 9 | −2 | 3 | 1 | −25 |
| 10 | −26 | −13 | −30 | −27 |
| 13 | −10 | −10 | −23 | −23 |

These results show the effectiveness of the compounds of formula I in inducing a decrease in the glycaemia in the diabetic animals.

Study of the Hypolipidaemic Activity in the Rat

The hypolipidaemic activity of the compounds of formula I by the oral route was determined on an experimental model of non-insulin-dependent diabetes induced in the rat by streptozotocin.

The model of non-insulin-dependent diabetes is obtained in the rats by a neonatal injection (5 days after birth) of streptozotocin.

The diabetic rats used are 6 months old. The animals are kept, from the day of their birth to the day of the experiment, in an animal house at a regulated temperature of 21 to 22° C. and are subjected to a fixed cycle of light (from 7 h to 19 h) and of darkness (from 19 h to 7 h).

Their diet consisted of a maintenance diet; water and food were provided "ab [sic] libitum", with the exception of the 18 hours of fasting preceding the withdrawals of the blood samples on which the lipid balances will be carried out.

The rats are treated by the oral route with the compound of Example 1 for 7 days. A 300-μl sample is withdrawn 18 h after the final administration of this compound.

The total cholesterol was quantitatively determined by the CHOE/CHOD/POD Trinder method as an end point (Instrumentation Laboratory reagent [lacuna] on a Monarch plus analyser (Instrumentation Laboratory).

The total triglycerides were quantitatively determined by the GPO/Trinder method as an end point (Sigma Diagnostic reagent) on a Monarch analyser (Instrumentation Laboratory).

| CONDITIONS FOR CARRYING OUT THE TEST | TOTAL CHOLESTEROL (mg/dl) | TOTAL TRIGLYCERIDES (mg/dl) |
| --- | --- | --- |
| In the absence of treatment | 90 | 167 |
| By treatment with a compound of Example 1 | 79 | 102 |

These results clearly demonstrate the hypolipidaemic activity of the compounds of the invention.

What is claimed is:

1. A compound of formula I:

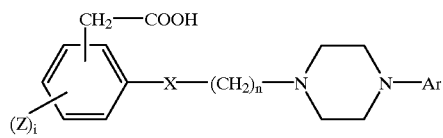

in which:

n represents 2, 3, 4, 5, or 6:

X represents O or S;

Ar represents phenyl, pyridyl, pyrimidyl, benzoxazolyl, benzothiazolyl or benzimidazolyl, optionally substituted by one or more radicals chosen from $(C_1–C_6)$ alkoxy; halogen; $(C_6–C_{10})$ aryloxy; $(C_6–C_{10})$aryl-$(C_1–C_6)$alkoxy in which the aryl part is optionally substituted by halogen, $(C_1–C_6)$alkyl or $(C_1–C_6)$ alkoxy; and $(C_1–C_6)$ alkyl substituted by one or more halogen atoms;

i represents 0, 1, 2, 3 or 4; and each Z group independently represents a halogen atom; or an addition salt thereof with a pharmaceutically acceptable base or acid.

2. A compound according to claim 1, in which X represents an oxygen atom.

3. A compound according to claim 1, wherein n represents 2 or 3.

4. A compound according to claim 1, wherein Ar represents pyridyl; pyrimidinyl; benzoxazolyl; benzothiazolyl; benzimidazolyl; phenyl; or phenyl substituted by one or more radicals chosen from $(C_1–C_6)$ alkoxy; halogen; phenoxy; trifluoromethyl and benzyloxy.

5. A compound according to claim 1, wherein Ar represents phenyl substituted in the meta position by $(C_1–C_6)$ alkoxy, a halogen atom, phenoxy or trifluoromethyl.

6. A compound according to claim 1, wherein i represents 0.

7. A compound according to claim 1, wherein the —CH$_2$—COOH group is in the para position on the phenyl group with respect to the chain:

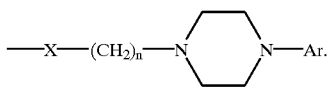

8. A process for preparation of a compound according to claim 1, comprising reacting an aromatic compound of formula II:

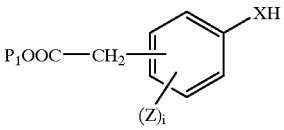

in which Z, X and i are as defined in claim 1 for the formula I and P$_1$ is a protective group for carboxyl functional group, with a piperazine of formula III:

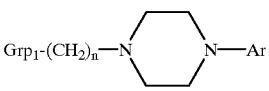

in which Ar and n are as defined in claim 1 for the formula I and Grp$_1$ is a leaving group, to obtain a compound of formula IV:

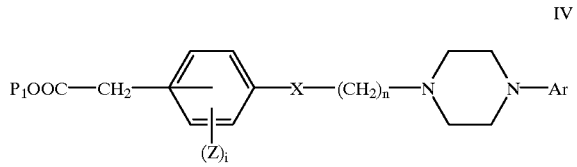

in which P$_1$, X, Z, i, n and Ar are as defined above, and converting the compound of formula IV to a compound of formula I by deprotection of the carboxyl functional group.

9. A process for preparation of a compound according to claim 1, comprising: reacting a piperazine of formula V:

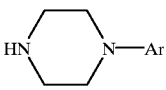

in which Ar is as defined in claim 1 for the formula I, with a carboxyl derivative of formula VI

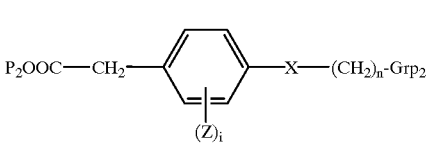

in which n, Z, X and i are as defined in claim 1 for the formula I, P$_2$ represents a protective group for carboxyl functional group and Grp$_2$ represents a leaving group, to obtain a compound of formula VII:

VII

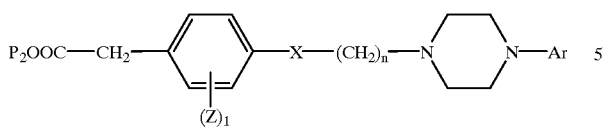

in which n, X, Z, Ar, i and $P_2$ are as defined above, and converting the compound of formula VII to a compound of formula I by deprotection of the carboxyl functional group.

10. A pharmaceutical composition comprising one or more compounds according to claim 1, in combination with at least one pharmaceutically acceptable excipient.

11. A method for the treatment of pathologies associated with insulin-resistance syndrome, comprising administering to a patient in need thereof an effective amount of a compound according to claim 1.

12. A method according to claim 11, wherein said patient is suffering from diabetes, dyslipidaemia, obesity, arterial hypertension, neuropathies, retinopathies or atherosclerosis.

13. A compound according to claim 3, wherein n is 2.

14. A compound according to claim 1, wherein the aryl part of aryloxy and arylalkoxy is phenyl or naphthyl.

15. A compound according to claim 1, wherein Ar is mono-, di- or tri-substituted phenyl.

16. A compound according to claim 1, wherein Ar is unsubstituted pyridyl, unsubstituted pyrimidinyl, unsubstituted phenyl, or substituted phenyl.

17. A compound according to claim 1, wherein Ar is phenyl having 1 to 2 substituents selected from $(C_1-C_6)$ alkoxy, halogen, phenoxy, trifluoromethyl, and benzyloxy.

18. A compound according to claim 1, wherein Ar is phenyl substituted in the meta position by $(C_1-C_6)$ alkoxy, fluorine, chlorine, phenoxy or trifluoromethyl.

19. A compound according to claim 1, wherein i is 1 or 0.

20. A compound according to claim 1, wherein i is 1 and the —$CH_2$—COOH group is in the ortho position with regard to the chain

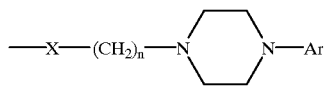

and Z is the para position with respect to this chain.

21. A compound of formula I:

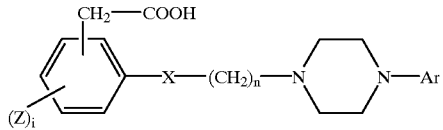

in which:

n represents 2, 3, 4, 5, or 6:

X represents O or S;

Ar represents phenyl, pyridyl, pyrimidyl, benzoxazolyl, benzothiazolyl or benzimidazolyl, optionally substituted by one or more radicals chosen from $(C_1-C_6)$ alkoxy; halogen; $(C_6-C_{10})$ aryloxy; $(C_6-C_{10})$aryl-$(C_1-C_6)$ alkoxy in which the aryl part is optionally substituted by halogen, $(C_1-C_6)$ alkyl or $(C_1-C_6)$ alkoxy; and $(C_1-C_6)$ alkyl substituted by one or more halogen atoms;

i represents 0, 1, 2, 3 or 4; and each Z group independently represents a halogen atom; or an addition salt thereof with a base or acid.

22. A compound according to claim 1, wherein the —$CH_2$—COOH group is in the para or ortho position with respect to the chain

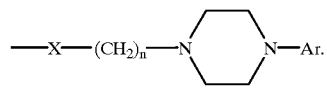

23. A compound according to claim 22, wherein the —$CH_2$—COOH group is in the para position with respect to the chain

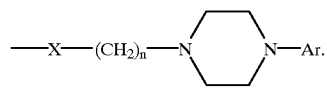

* * * * *